United States Patent [19]

Stutz, Jr.

[11] Patent Number: 5,012,807
[45] Date of Patent: May 7, 1991

[54] MULTI-PART MOLDED PACEMAKER CONNECTOR AND METHOD OF MAKING SAME

[75] Inventor: William H. Stutz, Jr., Burbank, Calif.

[73] Assignee: Siemens-Pacesetter, Inc., Sylmar, Calif.

[21] Appl. No.: 518,618

[22] Filed: May 3, 1990

[51] Int. Cl.$^5$ ............................................. A61N 1/375
[52] U.S. Cl. .................................................. 128/419 P
[58] Field of Search .................................... 128/419 P

[56] References Cited

U.S. PATENT DOCUMENTS

| | | | |
|---|---|---|---|
| 2,965,734 | 12/1960 | Timmerman | 200/144 |
| 3,571,547 | 3/1971 | Boersma et al. | 200/166 |
| 3,760,332 | 9/1973 | Berkovits et al. | 339/66 R |
| 4,072,154 | 2/1978 | Anderson et al. | 128/419 P |
| 4,182,345 | 1/1980 | Grose | 128/419 P |
| 4,469,104 | 9/1984 | Peers-Trevarton | 128/419 P |
| 4,684,202 | 8/1987 | House et al. | 439/752 |
| 4,712,557 | 12/1987 | Harris | 128/419 P |
| 4,715,380 | 12/1987 | Harris | 128/419 P |
| 4,764,132 | 8/1988 | Stutz | 439/810 |
| 4,848,346 | 7/1989 | Crawford | 128/419 P |
| 4,934,366 | 6/1990 | Truex et al. | 128/419 P |

FOREIGN PATENT DOCUMENTS

| | | |
|---|---|---|
| 0052879 | 6/1982 | European Pat. Off. . |
| 2383532 | 11/1978 | France ........................... 128/419 P |
| 29822 | of 1914 | United Kingdom . |

OTHER PUBLICATIONS

Calfee et al., "A Voluntary Standard for 3.2 mm Unipolar and Bipolar Pacemaker Leads and Connectors", Pace, vol. 9, pp. 1181-1185 (Nov.-Dec. 1986, Part II).

Primary Examiner—William E. Kamm
Attorney, Agent, or Firm—Bryant R. Gold; Lisa P. Weinberg; Malcolm J. Romano

[57] ABSTRACT

A multi-part molded pacemaker connector meets the precise requirements imposed by the VS-1 standard, yet does not require complex nor expensive machining of individual parts. The connector includes a molded body tip and a molded body ring, adapted to be joined together during assembly. The body tip is molded to include a conductive connector block attached to a first conductive ribbon as an integral part thereof. The body ring is molded to include a second conductive ribbon, having a looped end exposed therewithin to provide a precise specified diameter against which a garter spring contact is placed. An inner shoulder molded within the body ring holds the spring contact laterally on one side. During assembly, an annular spacer is pressed into the body ring to restrain the spring contact laterally on the other side. Inner and outer annular seals are also inserted into the body tip and body ring during assembly. After assembly, i.e., after joining the body tip to the body ring, the connector may be pretested for leakage, dimensionality and conductivity prior to casting it in epoxy as part of the pacemaker connector top.

20 Claims, 3 Drawing Sheets

MULTI-PART MOLDED PACEMAKER CONNECTOR AND METHOD OF MAKING SAME

BACKGROUND OF THE INVENTION

The present invention relates to implantable pacemakers, and more particularly to a connector used by an implantable pacemaker that allows a pacing lead to be detachably, yet reliably, connected to the pacemaker. Even more particularly, the present invention relates to a pacemaker connector made in compliance with precise industry imposed standards, but made in a way that does not require expensive, precision parts, nor a complex assembly or manufacture.

A pacemaker is a medical device that selectively provides stimulation pulses to the heart, or other body tissue, for the purpose of causing a desired muscle contraction. When properly used, a pacemaker can maintain a desired heart rate, causing the heart to beat so as to maintain the efficient flow of blood through a patient's body.

Modern pacemakers are made to be implanted in a patient, typically in a "pocket" of fatty tissue near the patient's upper breast or lower abdomen. As such, the electronic circuits used within a pacemaker (or "pacer") are hermetically sealed in a suitable housing, compatible with body tissue. Electrical connection is made with the pacemaker circuits via feedthrough terminals that pass through the hermetically sealed housing. These feedthrough terminals are then electrically connected to a "pacemaker connector", which pacemaker connector is attached to the pacemaker housing.

A pacemaker lead is used with an implantable pacemaker in order to maintain electrical contact between a desired tissue location and the pacemaker circuits. For cardiac pacing, such lead is typically inserted through one of the main veins of the patient, e.g., the superior vena cava, so that a distal end of the lead is directed inside of the heart. Electrodes positioned at the distal end of the lead make contact with the cardiac tissue. The proximal end of the pacemaker lead is then connected to the pacemaker connector.

The pacemaker connector typically takes the form of a female connector, with the proximal end of the pacemaker lead taking the form of a male connector. When joined together, good electrical contact must be maintained between a proximal electrode of the pacemaker lead and an appropriate feedthrough terminal of the pacemaker housing. Further, such connection must be secure, so that it does not disconnect during use, yet it must be detachable, in the event the pacemaker or lead needs to be replaced. Moreover, such connections must at all times remain insulated and sealed from body fluids, which body fluids are conductive and could cause an electrical short.

For single conductor pacemaker leads, the pacemaker connector has typically included a connector block having a recess or hole into which a proximal electrode pin of the pacing lead is inserted and secured with a set screw. Suitable means are then used to electrically connect the connector block to the pacemaker's feedthrough terminal. The connector block is then cast into a suitable "header assembly" that is bonded to the pacemaker housing. The cast header assembly both insulates the connector block from body fluids, and positions the header block so as to properly receive the proximal electrode of the pacer lead.

For multi-conductor pacemaker leads, e.g., bipolar pacing leads, one or more proximal ring electrodes of the pacing lead must also make secure electrical contact with an appropriate feedthrough terminal on the pacemaker housing. Numerous schemes have been proposed and used over the years to achieve this purpose, with varying degrees of success. See, e.g., U.S. Pat. No. 4,764,132 (an earlier patent of Applicant's directed to the problem of making a secure electrical connection to the delicate proximal ring electrode of a pacing lead using a set screw without deforming the proximal ring electrode).

Thus, over the approximately 30 year history of implantable pacemakers, a wide variety of techniques and methods have been used to connect leads to pacemakers. Many of these methods and techniques are no longer suitable for the smaller pacemakers and leads that are currently being used.

Recently, an effort has been underway to standardize the interface between a pacemaker lead and a pacemaker. See, e.g., Calfee, et al., "A Voluntary Standard for 3.2 mm Unipolar and Bipolar Pacemaker Leads and Connectors," PACE, Vol. 9, 1181-85 (Nov.-Dec. 1986). The standard therein proposed, referred to as the VS-1 (voluntary standard-1), has subsequently been adopted by almost all pacemaker manufacturers worldwide. The VS-1 standard does not specify how a particular pacemaker connector must make contact with a pacemaker lead, it simply defines the dimensions of the pacemaker lead and the dimensions of the pacemaker connector cavity into which the pacemaker lead is inserted. The VS-1 standard further specifies certain requirements as to leakage, conductivity and connection/disconnection force. While the VS-1 standard advantageously represents a long needed movement towards industry standardization, when translated to a particular type of pacemaker connector design, the VS-1 standard disadvantageously sets some rather stringent manufacturing tolerances. Such stringent manufacturing tolerances have heretofore only been obtainable using labor intensive, expensive manufacturing techniques, e.g., machining of individual parts. What is needed, therefore, is a pacemaker connector that meets the VS-1 standard, and that also can be made using less labor-intensive and less expensive manufacturing methods and techniques.

The present invention advantageously addresses this and other needs.

SUMMARY OF THE INVENTION

In accordance with one aspect of the present invention, there is provided a pacemaker connector that meets the precise requirements imposed by the VS-1 standard (or any other applicable standard), yet that does not require complex nor expensive machining of individual parts. Advantageously, the pacemaker connector includes multiple parts, each of which is inexpensively made, e.g., by molding, or is purchased or otherwise acquired for subsequent assembly. One of the molded parts is a body tip. Another is a body ring. The body tip is molded to include a conductive connector block attached to a first conductive ribbon. A pigtail of the first conductive ribbon protrudes out from the molded body tip. The body ring is molded to include a second conductive ribbon having a hoop end exposed therewithin to provide a precise specified diameter. A pigtail of the second conductive ribbon protrudes out from the molded body ring.

During assembly of the pacemaker connector, a garter spring contact is inserted within the body ring so as to make circumferential contact with an inner surface of the exposed hoop. An inner shoulder molded within the body ring prevents the garter spring from moving laterally off of the exposed hoop in one direction. An annular spacer inserted into the body ring after insertion of the garter spring prevents it from moving laterally off of the exposed hoop in the other direction. Sealing rings, adapted to provide a tight seal around a pacemaker lead inserted into the connector, are further inserted into the body tip and the body ring during assembly. The body ring is then joined to the body tip, to form the completed pacemaker connector assembly.

Advantageously, after assembly of the pacemaker connector, i.e., after joining the body tip to the body ring, the pacemaker connector may be pretested for leakage, dimensionality and conductivity. If these tests are successfully passed, then the pigtails of the first and second conductive ribbons are welded, or otherwise bonded, to appropriate feedthrough terminals of a hermetically sealed pacemaker housing (pacemaker "can"), and the pacemaker connector is then cast into a pacemaker header assembly that is bonded to the pacemaker can as part of the final pacemaker assembly. The epoxy casting of the header assembly advantageously maintains the pigtails of the pacemaker connector in a suitable spaced-apart relationship during operation of the pacemaker, thereby preventing any electrical shorts therebetween.

One embodiment of the invention may thus be characterized as a multi-part pacemaker connector that includes: (1) a molded body tip including a connector block and first conductive means for making electrical contact with the connector block, the connector block and at least a portion of the first conductive means being molded into the body tip so as to form an integral part thereof; (2) a molded body ring including second conductive means, the second conductive means having a hoop at one end thereof that defines an exposed precision inner diameter within the body ring, the hoop end of the second conductive means being molded into the body ring so as to form an integral part thereof; (3) a conductive garter spring sized to slide into the molded body ring; (4) means for maintaining the garter spring in physical contact with the exposed inner diameter of the hoop end of the second conductive means, thereby allowing the garter spring to make electrical contact with the second conductive means; and (5) means for joining the molded body tip to the molded body ring. Such connector advantageously allows first and second spaced apart proximal electrodes of a pacemaker lead to be inserted into the pacemaker connector and make respective electrical contact with the block electrode and with the garter spring, thereby allowing electrical contact to be made with the first and second proximal electrodes of the pacing lead via the first and second conductive means, respectively.

A further embodiment of the invention may be characterized as a pacemaker connector assembly that includes a pacemaker connector as above-described, and further includes means for making respective electrical contact between the first and second conductive means of the pacemaker connector to first and second pacemaker feedthrough terminals of a sealed pacemaker housing. Such electrical contact is advantageously realized by simply welding or otherwise securing the first and second conductive means of the pacemaker connector, each of which has a pigtail that protrudes from the molded pacemaker connector, to the first and second pacemaker terminals. The pacemaker connector and pigtails are then cast in epoxy, or equivalent, and bonded to the pacemaker housing.

A further embodiment of the invention may be characterized as a method of inexpensively making a molded pacemaker connector that includes a precise inner dimension, needed, e.g., to meet the stringent requirements imposed by the VS-1 standard used by pacemaker manufacturers. Such method includes: (a) forming a hoop in a first end of a first electrical conductor, this hoop having a non-precise diameter that is somewhat less than a precision diameter required in the pacemaker connector; (b) expanding the hoop end of the first electrical conductor over a precision core pin within a connector mold, the precision core pin having a diameter equal to the precision diameter; (c) injecting a non-conductive polymer, such as polysulfone, manufactured by Amoco Performance Products of Ridgefield, Conn., into the connector mold while the polymer is in a liquid state, and allowing the polymer to cure to assume a solid state; and (d) removing the cured polymer, including the first electrical conductor, from the connector mold, the hoop end of the electrical conductor being held to the precision diameter by the cured polymer, a second end of the first electrical conductor protruding out from the cured polymer as a pigtail. This cured polymer, including the hoop end of the electrical conductor molded therein, may thereafter be used as a component of a pacemaker connector assembly wherein such precise diameter is required.

It is a feature of the present invention to provide a pacemaker connector, and method of making a pacemaker connector, that meets the VS-1 standard or any other standards that may be imposed, such as the proposed ISO DIS 5841-3 standard, presently under consideration by the Food and Drug Administration.

It is a further feature of the invention to provide such a connector that is easy and inexpensive to manufacture and assemble, avoiding the necessity of machining individual parts in order to obtain precision dimensions.

It is another feature of the invention to provide such a pacemaker connector that may be used with either pacemaker leads having seals (VS-1B) or not having seals.

It is still another feature of the invention to provide such a pacemaker connector that can be pretested for leakage, conductivity and dimensionality prior to being casted into a pacemaker header assembly.

It is yet an additional feature of the invention to provide a pacemaker connector that is made from a plurality of individually molded parts, with each individual part being designed to readily allow the insertion of seals and other connector components, prior to joining the parts together. That is, it is a feature of the invention to provide a pacemaker connector design that facilitates its assembly.

It is yet another feature of the invention to provide a pacemaker connector utilizing a "canted coil garter spring" to make electrical contact around the entire periphery of a proximal electrode, e.g., a proximal ring electrode, of a pacemaker lead, thereby maintaining a safe, reliable and secure electrical connection.

It is a further feature of the invention to provide a method of making a multi-part pacemaker connector that assures a good tight fit between the individual components thereof.

BRIEF DESCRIPTION OF THE DRAWINGS

The above and other features and advantages of the present invention will be more apparent from the following more particular description thereof presented in conjunction with the following drawings wherein.

DETAILED DESCRIPTION OF THE INVENTION

The following description presents the best mode contemplated for practicing the invention. This description is not to be taken in a limiting sense but is made merely for the purpose of describing the general principles of the invention. The scope of the invention should be ascertained with reference to the claims.

The present invention will be explained with reference to the above-described figures, wherein like numerals are used to represent like parts or elements throughout.

Figure 1:
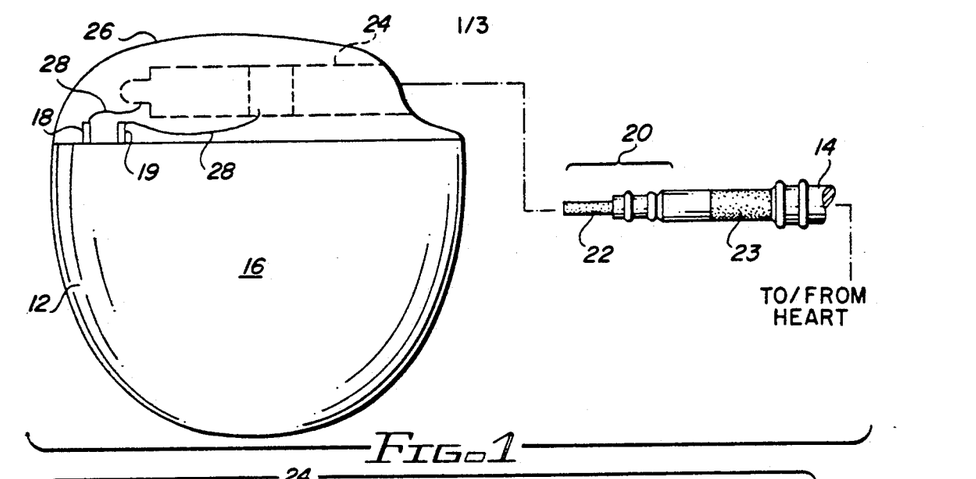
FIG. 1 diagrammatically depicts the main elements of a pacemaker system, including a pacemaker and a pacemaker lead.

Referring first to FIG. 1, there is shown a diagram of the main elements of a pacemaker system, including a pacemaker 12 and a pacemaker lead 14. The pacemaker 12 includes a hermetically sealed housing 16, inside of which the pacemaker electronic circuits and battery are housed. Electrical contact is made with the electronic circuits by means of one or more feedthrough terminals 18, 19. In some models of pacemakers, the sealed housing 16 (frequently referred to as the pacemaker "can") is made from an electrically conductive material, and electrical contact may also be made through an exposed (non-insulated) portion of the conductive material of the can.

A proximal tip 20 of the pacing lead 14 includes one or more terminals 22, 23 that make respective electrical contact with the feedthrough terminals 18, 19 of the pacemaker. This electrical connection is facilitated through the use of a pacemaker connector 24, the outline of which is shown in FIG. 1 as a dotted line within a pacemaker header assembly 26. The pacemaker connector 24, explained in more detail below, is placed within the header assembly 26 so as to receive the proximal tip 20 of the pacing lead 14. The header assembly 26, in turn, is fastened to the top of the pacer can 16. Means 28, e.g, such as wires or conductive ribbons, are included in the header assembly for making electrical contact between appropriate terminals of the connector 24 and the feedthrough terminals 18, 19.

In use, the proximal tip 20, functioning as a "male" connector, slides inside of the pacemaker connector 24, functioning as a "female" connector. Once in position within the connector 24, the proximal electrodes 22, 23 of the pacing lead 14 make electrical contact with corresponding terminals inside of the connector 24, which terminals, in turn, are in respective electrical contact with the feedthrough terminals 18, 19. It is the function of the pacemaker connector 24 to allow a reliable, yet detachable, electrical contact to be maintained between the proximal tip electrodes 22, 23 and the feedthrough terminals 18, 19.

It is noted that the pacemaker connector invention described herein is described in terms of a bipolar connection. That is, the invention is described with reference to the use of a bipolar pacing lead, i.e., a pacing lead having two separate conductors, one connected to a proximal tip electrode 22, and the other connected to a proximal ring electrode 23. However, it is to be understood that various aspects of the invention also have applicability to unipolar pacing (single conductor leads), or multi-polar pacing (multiple conductor leads).

Figure 2A:
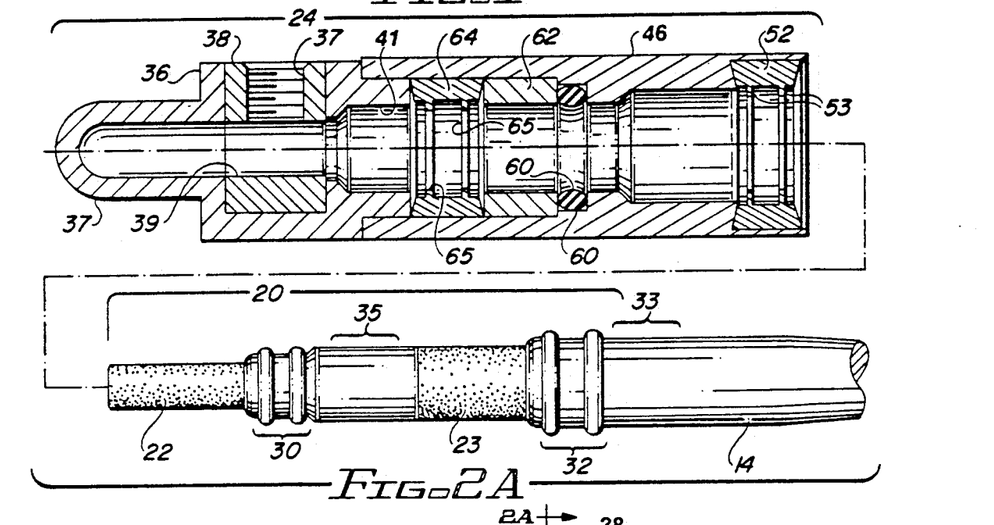
FIG. 2A is a sectional view of a pacemaker connector made in accordance with the present invention, and further illustrates a side profile view of the proximal end of a pacemaker lead adapted to be inserted into the pacemaker connector.
Figure 2B:
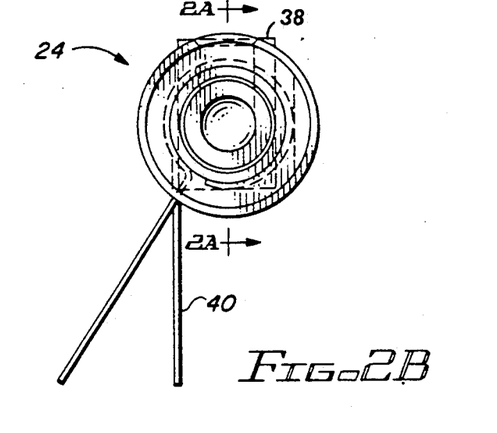
FIG. 2B is an end view of the pacemaker connector shown in FIG. 2A.

Referring next to FIGS. 2A and 2B, there is shown a sectional view and an end view, respectively, of the pacemaker connector 24 made in accordance with the present invention. FIG. 2A further illustrates a side profile view of the proximal end 20 of a pacemaker lead 14 made in accordance with the VS-1 standard and adapted to be inserted into the pacemaker connector 24. This side profile of the proximal tip 20 also shows two sets of sealing rings 30 and 32 that may be optionally included on a VS-1 lead.

Figures 3, 4A, 4B:
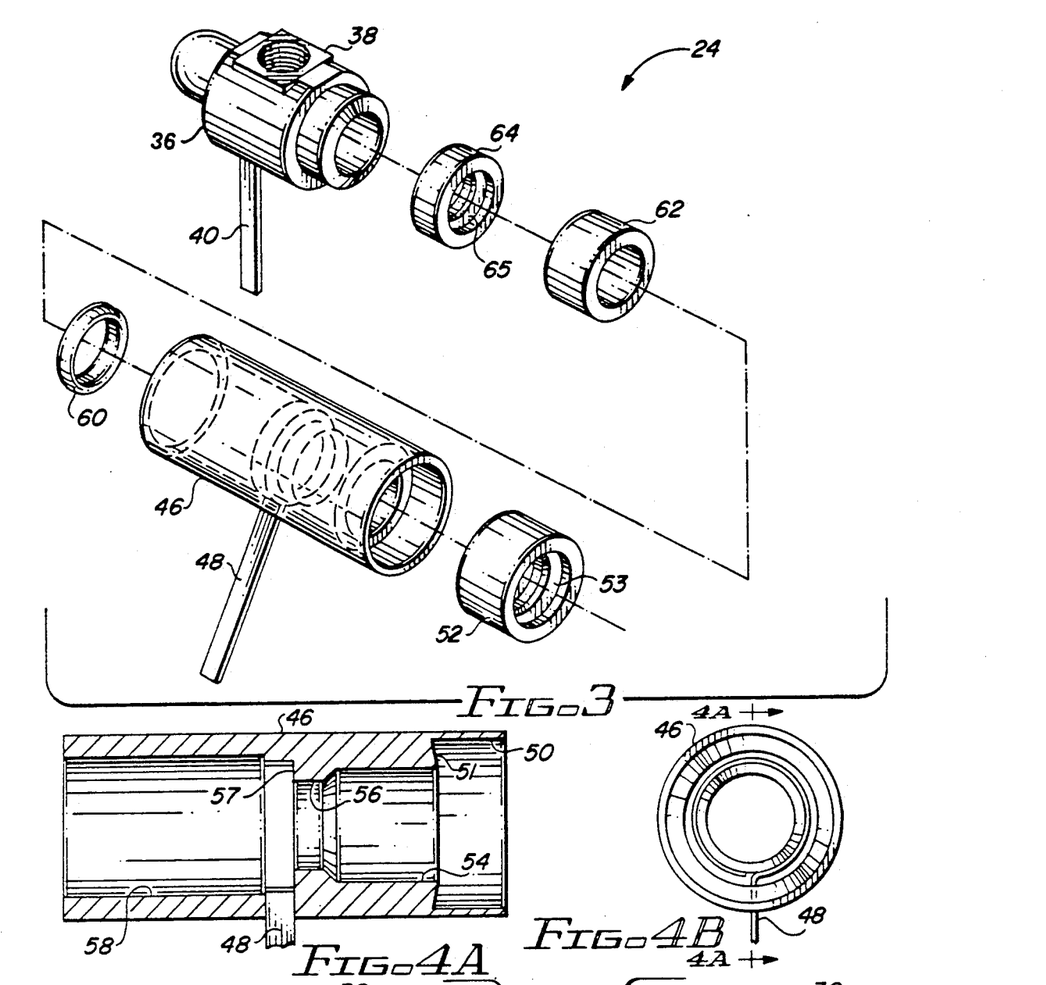
FIG. 3 is an exploded view of the pacemaker connector shown in FIGS. 2A and 2B.
FIGS. 4A and 4B are sectional and end views, respectively, of the body ring portion of the pacemaker connecter shown in FIGS. 2A and 3.

The individual components of the pacemaker connector 24 are best seen in the exploded view of the pacemaker connector shown in FIG. 3. However, many of the details associated with these components, as well as their manner of assembly, can also be ascertained from the other figures. Hence, in the discussion that follows, reference should be made to whichever figure(s) best depicts the particular element(s) being described. The same numerals will be used to describe the same parts throughout.

Figures 5A, 5B:
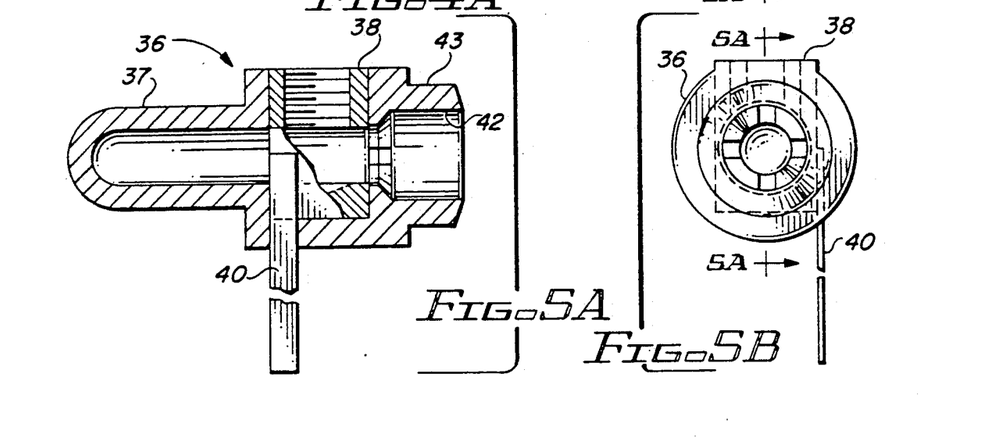
FIGS. 5A and 5B are sectional and end views, respectively, of the body tip portion of the pacemaker connector shown in FIGS. 2A and 3.

As best seen in FIG. 3, the pacemaker connector 24 includes a body tip 36 and a body ring 46. Sectional and end views of the body tip 36 are shown in FIGS. 5A and 5B, respectively. Sectional and end views of the body ring 46 are shown in FIGS. 4A and 4B, respectively. Both of these parts are molded parts, thereby facilitating their manufacturability. Both of these parts have a main channel or opening through which (body ring 46) or into which (body tip 36) the proximal tip 20 passes or enters when inserted into the pacemaker connector 24.

A tip connector block 38, made from a conductive material compatible with body fluids, such as stainless steel, is molded into the body tip 36. The tip connector block 38 has a hole or channel 39 drilled therethrough. The tip electrode 22 is received in this channel 39 when the proximal tip 20 is inserted into the connector 24. Another hole or channel 41, transverse to the channel 39, is threaded so as to receive a set screw (not shown). Hence, when the tip electrode 22 is inserted into the channel 39, the set screw may be tightened in conventional manner in order to firmly secure the electrode 22 to the connector block 38.

A conductive ribbon 40 is secured to the connector block 38 prior to molding the connector block within the body tip 36. One end of this ribbon 40 protrudes out from the body tip 36 as a "pigtail", which pigtail provides the means for making electrical connection with the appropriate feedthrough terminal on the pacemaker housing when the connector is cast into the connector top 26.

It is noted that other means may be used to secure the proximal tip electrode 22 within the pacemaker connector 24 other than the conventional set screw and connector block configuration described above. For example, a set screwless connection scheme may be employed using two garter springs, one for contacting the tip electrode 22, the other for contacting the ring electrode 23.

The body tip 36, as seen best in FIG. 5A, is open at one end and closed at the other end. A tip portion 37 at the closed end provides a recess internal to the body tip 36 where a portion of the tip electrode 22 of the pacing lead 14 may reside. A recess 42 provides a smooth inner surface against which the sealing rings 30 of the proximal tip 20 may act to form a fluid-tight seal. A circumferential protruding shoulder 43 provides a surface or stub that is inserted into the body ring 46 when the body ring is joined to the body tip.

The body ring, as seen best in FIG. 4A, is open at both ends. The body ring is also a molded part. Approximately in the middle of the body ring is a conductive ribbon 48 having one end formed in a circle or hoop. The hoop end of the ribbon 48 is molded into the body ring 46 so as to assume a precise diameter, as explained below. The other end of the ribbon 48 protrudes out from the body ring 46 as a second "pigtail." This pigtail provides the means for making electrical contact with the appropriate feedthrough terminal of the pacemaker housing when the connector is cast into the header assembly 26.

At the front end of the body ring 46, i.e., that end not joined to the body tip 36, there is a first recess 50. This recess is dovetailed, as shown at 51. This first dovetailed recess is designed to receive a first annular inner seal 52. This inner seal 52, as best seen in FIG. 3, and sometimes referred to as an entrance seal, is shaped like a ring or doughnut, having inner circumferential ridges 53 adapted to make sealing contact with the smooth surface 33 of the pacing lead 14.

A second recess 54 is adjacent to the dovetailed recess 50, having a smaller diameter than the recess 50. It is the function of this second recess 54 to provide a smooth surface against which the sealing ridges 32 of the pacing lead 14 may make sealing contact. (Note from the sectional view of FIG. 4A that the recesses 50 and 54 have the appearance of counterbores having differing diameters. However, because the use of the term "counterbore" could imply that the counterbore is machined into the particular part wherein the counterbore is found, and whereas the recesses 50 and 54 are not machined, but are formed during the molding process of the body tip 36, the term "counterbore" is not used herein.)

As still seen best in FIG. 4A, moving rearward through the body ring 46 (i.e., right-to-left as drawn in FIG. 4A), there is next found a narrow neck 56. This neck 56 defines a diameter that is just large enough for the proximal ring electrode 23 to pass therethrough, but sufficiently small to prevent the sealing rings 32 from passing therethrough. The hoop end of the conductive ribbon 48, with a somewhat larger diameter than the recess 54, is adjacent the neck 56. On the side of the hoop opposite the neck 56, a third recess or inner channel 58 is found having a diameter slightly larger than the hoop end of the conductor 48, but less than the diameter of the first recess 50.

As seen best in FIGS. 2A and 3, during assembly, a conductive garter spring 60 is inserted into the recess 58, from the back end (i.e., that end adapted to be joined to the body tip 36) of the body ring 46 so as to abut the shoulder 57 separating the narrow neck portion 56 from the hoop end of the conductive ribbon 48. In this position, the garter spring 60 advantageously makes circumferential contact with the inner surface of the conductive hoop. The dimensions of the garter spring are such that its inner diameter protrudes into the channel through the body tip somewhat more than the narrow neck 56. This is a slightly smaller diameter than the outer diameter of the proximal ring electrode. Hence, when the proximal tip 20 is inserted into the connector 24, the proximal ring electrode compresses the garter spring somewhat in order to expand its diameter to allow the proximal ring electrode 23 to fit therein. This compression advantageously assures that the garter spring 60 surrounds and makes good multi-point electrical contact around the entire circumference of the proximal ring electrode 23. At this same time, this compression also assures that the outer diameter surface of the garter spring 60 is pushed against and makes good multi-point electrical contact with the entire inner circumference of the hoop end of the ribbon conductor 48.

The shoulder 57 prevents lateral movement of the garter spring 60 in a forward direction within the body ring 46. A spacer 62 is pressed into the body ring 46 to prevent lateral movement of the garter spring in a rearward direction. The rear edge of the spacer 62 is angled, e.g., chamfered at 15 degrees, as is the front edge of the shoulder 43, so as to form a dovetailed recess into which a second annular inner sealing ring 64 is inserted when the body tip 36 is joined to the body ring 46. Of course, the second annular inner sealing ring 64 is inserted into the body ring 46 prior to joining the body ring to the body tip, thereby facilitating assembly of the pacemaker connector. The second inner sealing ring 64 has a pair of inwardly protruding sealing ridges 65 adapted to make sealing contact with the smooth surface 35 of the pacing lead 14 when the proximal tip 20 of the lead is inserted into the connector.

Prior to injection molding of the body tip 36 and the body ring 46, the conductive ribbon 40 is bonded (e.g., welded) to the connector block 38, and one end of the conductive ribbon 48 is formed into a hoop having an arbitrary size somewhat less than the precision size required for a good interface with the garter spring 60. (This conductive ribbon 48 with a hoop formed in one end is sometimes referred to as a "shepard's crook".) The conductive block 38, with conductive ribbon welded thereto is then seated in the appropriate mold for the body tip 36. The hoop end of the shepard's crook is then forced over a precision diameter core pin in the appropriate mold for the body ring 46. The injection molding process is then carried out in conventional manner. As the polysulfone (or other equivalent material) cures, the connector block is permanently held in its prescribed position within the body tip 36, and the hoop end of the conductive ribbon 48 is permanently held in its prescribed position within the body ring 46 at the prescribed diameter defined by the precision core pin in the mold. Advantageously, this process allows a precision diameter to be obtained in the hoop end of the conductive ribbon 48 without the necessity of machining each individual part. (Only the core pin in the mold need be machined, and that is a one-time operation.)

It is noted that a precision diameter is required in the hoop end of the conductive ribbon 48 in order for the garter spring 60 to perform its intended function of making a reliable and secure electrical contact with both the proximal ring electrode 23 and the conductive ribbon 48. A suitable garter spring 60 may be obtained commercially from Bal Seal Engineering Company, Inc., of Santa Ana, Calif., and is also known as a "canted coil" spring, or a "canted coil garter spring".

After molding the body tip 36 and the body ring 46, the garter spring 60, spacer 62, and inner seal 64 are slid into position within the body ring 46, and the body tip 36 is joined to the body ring 46. These parts are molded so that a secure press fit is obtained when they are joined, with the shoulder 43 of the body tip 36 tightly fitting within the channel 58 of the body ring 46. After joining, the entrance seal 53 is slid or pushed into position at the front end of the connector 24.

After the connector 24 has been assembled as described above, it can be pretested for leakage, dimensionality, conductivity, as well as for any other specified parameters, such as proper insertion/removal forces. This ability to pretest the connector significantly improves the yield of the overall pacemaker manufacturing process. Further, the multipart nature of the connector 24 allows the connector to be inexpensively manufactured.

Once the connector 24 has been assembled and tested as described above, the connector is properly positioned above the pacemaker housing 16 (using an appropriate header assembly mold or fixture guide), and the two pigtails (one comprising the free end of the conductive ribbon 40, and the other comprising the free end of the conductive ribbon 48), are folded appropriately so as to make electrical contact with the feedthrough connectors 18 and 19, respectively. In so doing, care must be exercised to make sure these two conductive ribbons do not touch each other. Preferably, the ends of the ribbons 40 and 48 are welded, or otherwise permanently bonded, to the terminals 18 and 19. Once so attached, the pacemaker connector top 26 is completed by casting the connector assembly in a biocompatible epoxy, such as Hysol, which epoxy also serves to bond the connector top 26 to the pacemaker can 16.

It is noted that the seals 52 and 64 are preferably made from a flexible silicon elastomer, having a 70A shore hardness. The conductive ribbons 40 and 48 are preferably made from 316L stainless steel. The garter spring 60 is made from a suitable conductive spring material, such as MP35N alloy.

The dimensions for the pacemaker connector 24, including the component parts used therein, are dictated by the particular connector standard, or other connector specification, that is used. The VS-1 dimensions, for example, are published in the known literature.

Figure 6:
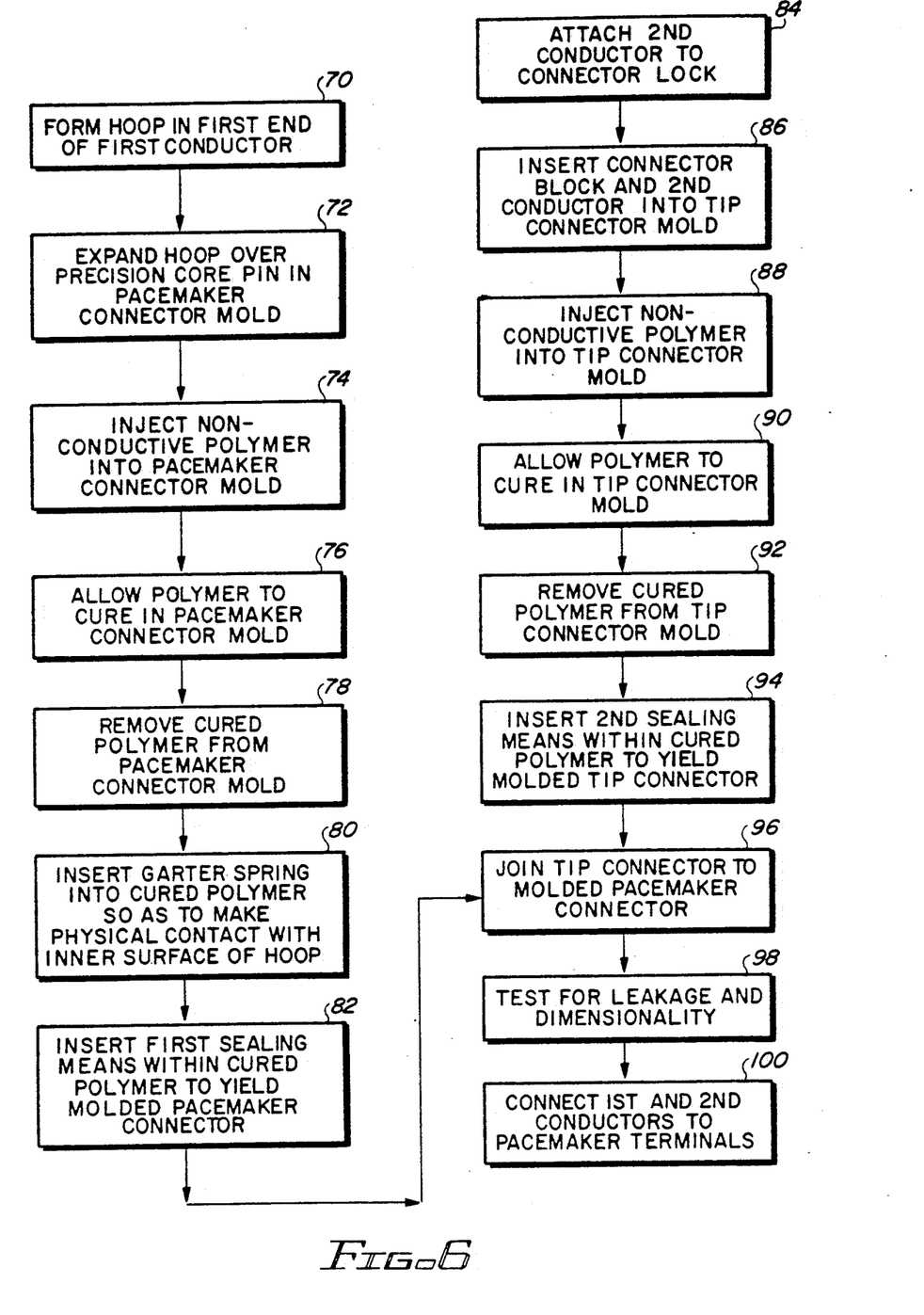
FIG. 6 illustrates the method of making a molded pacemaker connector in accordance with the present invention.

Referring next to FIG. 6, the method of making a molded pacemaker connector in accordance with the present invention is illustrated. The reference numerals in parenthesis are the same as are used in the description of FIGS. 1–5B above, or are used to identify particular "blocks" in FIG. 6.

As seen in FIG. 6, the method includes a first step (block 70 of FIG. 6) of forming a hoop in a first end of a first electrical conductor (48). This hoop has a diameter less than a precision diameter required in the pacemaker connector. A second step (block 72 of FIG. 6) involves expanding the hoop end of the first electrical conductor over a precision core pin within a pacemaker connector mold. The precision core pin has a diameter equal to the precision diameter. Next, the method calls for injecting a non-conductive polymer into the pacemaker connector mold (block 74 of FIG. 6) while the polymer is in a liquid state. A next step (block 76 of FIG. 6) allows the polymer to cure to assume a solid state. Then, the cured polymer, including the first electrical conductor, is removed from the pacemaker connector mold (block 78 of FIG. 6), with the hoop end of the electrical conductor being held to the precision inner diameter by the cured polymer, and with a second end of the first electrical conductor protruding out from the cured polymer. The cured polymer, including the hoop end of the electrical conductor molded therein, comprise the body ring (46).

The method of making a molded pacemaker connector as shown in FIG. 6 further includes inserting a garter spring (60) into the cured polymer so as to make physical contact with an inner surface of the hoop (block 80 of FIG. 6). The garter spring (60), as described above, is made from an electrically conductive material. The garter spring thus provides a means for making electrical contact between the first electrical conductor (48) and the circumference of an electrode (23) of a pacemaker lead (14) inserted into the body ring (46) so as to pass through the garter spring.

Finally, the method of making a molded pacemaker connector as shown in FIG. 6 further includes inserting a first sealing means (52) within the cured polymer (block 82 in FIG. 6). As previously described, this first sealing means seals the garter spring and hoop from coming in contact with fluids to which the molded pacemaker connector is externally exposed.

In addition to making a molded pacemaker connector as described, the method also contemplates attaching a second electrical conductor (40) to a connector block (38) adapted to receive a tip electrode (22) of a pacemaker lead (14), as indicated at block 84 of FIG. 6. The connector block, with the second electrical conductor attached thereto, is then inserted into a tip connector mold, as indicated at block 86 of FIG. 6. Thereafter, a non-conductive polymer is injected into the tip connector mold while the polymer is in a liquid state (block 88 of FIG. 6). The polymer is then allowed to cure to assume a solid state (block 90 of FIG. 6); after which the cured polymer, including the connector block (38) and second electrical conductor (40), are removed from the tip connector mold (block 92 of FIG. 6). The detached end of the second electrical conductor (40) protrudes out from the cured polymer. The cured polymer and the connector block molded therein thus comprise the body tip portion (36) of the molded pacemaker connector. As desired, a second sealing means (64) is inserted within the tip connector (36), as shown at block 94 of FIG. 6.

The method next involves joining the tip connector (36) to the molded pacemaker connector, or body ring (46), as indicated at block 96 of FIG. 6. Once theses two components are joined together, the combined components are tested for leakage and dimensionality (block 98 of FIG. 6). If such tests are passed successfully, then the method includes connecting the protruding ends of the first electrical conductor (48) and the second electrical conductor (40) to respective terminals (18, 19) of a sealed pacemaker (16). As a final step (not shown in FIG. 6), the method involves casting the tested molded pacemaker connector in an epoxy header assembly that is bonded to the sealed pacemaker in conventional manner.

As indicated above, in carrying out the above method, the non-conductive polymer used in steps 74 and 88 comprises polysulfone. Further, the first sealing means (52) and the second sealing means (64) are preferably made as an annular ring from a flexible silicon elastomer. Each such annular ring is made to have a plurality of circumferential ridges (53, 65) adapted to make sealing contact with the circumference of a pacemaker lead inserted into the molded pacemaker connector.

As described above, it is thus seen that the present invention provides a pacemaker connector, and method of making a pacemaker connector, that readily meets the stringent VS-1 standard (or any other standard that may be imposed), and yet is easy and inexpensive to manufacture and assemble, avoiding the necessity of machining individual parts in order to obtain precision dimensions. Advantageously, the pacemaker connector thus provided may be used with pacemaker leads having seals (VS-1B) or with pacemakers not having seals. Further, once assembled, the pacemaker connector can be pretested for leakage, conductivity and dimensionality prior to being cast into a pacemaker header assembly, thereby significantly improving the overall yield of the pacemaker assembly process.

The ease with which the pacemaker connecter herein described can be manufactured and assembled is due is large part to the fact that it is made from a plurality of individually molded parts. Each individual part advantageously is designed to readily allow the insertion of seals, garter springs, and other connector components, prior to joining the parts together. As also described above, it is seen that the present invention provides a pacemaker connector utilizing a "garter spring" to make electrical contact around the entire periphery of a proximal electrode, e.g., a proximal ring electrode, of a pacemaker lead. Such contact assures that a good electrical connection will be made and maintained, yet such contact (unlike a set screw) will not damage the proximal electrode. Further, such contact does not require any adjustments (as does a set screw), as the gripping force of the garter spring is controlled by the size of the garter spring and the dimension (diameter) of the recess within which the garter spring resides. Advantageously, as described above, this dimension is precisely maintained at a desired value by molding a conductive hoop into the body ring portion of the pacemaker connector. The inner surface of this conductive hoop defines the diameter of the recess wherein the garter spring resides, and this diameter is precisely set to the desired value by employing a precision core pin in the mold used to make the body ring portion of the connector.

While the invention described herein has been described with reference to specific embodiments and applications thereof, numerous variations and modifications could be made thereto by those skilled in the art without departing from the spirit and scope of the invention as claimed.

What is claimed is:

1. A multi-part pacemaker connector comprising:
   a molded body tip including a connector block and first conductive means for making electrical contact with said connector block, said connector block and at least a portion of said first conductive means being molded into said body tip so as to form an integral part thereof;
   a molded body ring including second conductive means, said second conductive means having a hook at one end thereof that defines an exposed precision diameter within said body ring, said hook end of said second conductive means being molded into said body ring so as to form an integral part thereof;
   a garter spring sized to slide into said molded body ring, said garter spring comprising an electrically conductive material;
   means for maintaining said garter spring in physical contact with the exposed diameter of the hook end of said second conductive means, whereby said garter spring makes electrical contact with said second conductive means; and
   means for joining said molded body tip to said molded body ring so as to form said multi-part pacemaker connector;
   whereby first and second spaced apart proximal electrodes of a pacemaker lead may be inserted into said pacemaker connector and make respective electrical contact with said block electrode and said garter spring;
   whereby electrical contact may be made with said first and second proximal electrodes of said pacing lead via said first and second conductive means, respectively.

2. The multi-part molded pacemaker connector as set forth in claim 1, wherein said means for maintaining said garter spring in physical contact with the exposed diameter of the hook end of said second conductive means comprises:
   an inner shoulder molded within the body ring to restrain lateral movement of the garter spring in one direction, and
   an annular spacer pressed into said body ring after said garter spring is slid into physical contact with the hook end of the second conductive means to restrain lateral movement of the garter spring in the other direction.

3. The multi-part molded pacemaker connector as set forth in claim 2 further including an inner annular seal inserted into said molded body tip, and an annular entrance seal inserted into said body ring, said inner and entrance seals having annular ridges for making sealable contact with a proximal end of said pacemaker lead when the first and second proximal electrodes of said pacemaker lead are inserted into said pacemaker connector.

4. The multi-part molded pacemaker connector as set forth in claim 1, wherein said first and second conductive means comprise first and second conductive ribbons, respectively.

5. The multi-part molded pacemaker connector as set forth in claim 4, wherein the hook end of said second conductive ribbon is initially formed to have a diameter smaller than the precision diameter that said hook end assumes when molded into said body ring, said hook end being expanded and held to said precision diameter when said body ring is molded.

6. The multi-part molded pacemaker connector as set forth in claim 5, wherein said pacemaker connector is sized to comply with VS-1 standards.

7. The multi-part molded pacemaker connector as set forth in claim 1, wherein said means for joining said molded body tip to said molded body ring comprises engagement means on one of said body tip or body ring for press fit engagement with the other of said body tip or body ring.

8. The multi-part molded pacemaker connector as set forth in claim 7, wherein said engagement means includes an annular lip protruding from said molded body tip sized for a press fit within said molded body ring.

9. The multi-part molded pacemaker connector as set forth in claim 1, wherein said molded body tip and molded body ring are molded from polysulfone.

10. A pacemaker connector assembly for detachably, electrically connecting first and second spaced-apart electrodes of a pacemaker lead to first and second terminals of an implantable pacemaker, said pacemaker connector assembly comprising:
   a nonconductive body tip having a connector block molded therein, said connector block including means for receiving said first electrode of said pacemaker lead, said body tip further including first conductive means for making electrical contact with said connector block, at least a portion of said first conductive means also being molded into said body tip;
   a nonconductive body ring having second conductive means, said second conductive means having a hook at one end thereof that defines an exposed precision diameter within said body ring, said hook end of said second conductive means being molded into said body ring;
   a garter spring sized to fit into said molded body ring, said garter spring comprising an electrically conductive material;
   means for maintaining said garter spring in physical contact with the exposed diameter of the hook end of said second conductive means, whereby said garter spring makes electrical contact with said second conductive means; and
   means for making respective electrical contact between said first and second conductive means to said first and second pacemaker terminals;
   whereby said first and second spaced apart electrodes of said pacemaker lead may be inserted into said body tip and body ring so as to make respective electrical contact with said block electrode and said garter spring;
   whereby electrical contact is made between said first and second electrodes of said pacing lead and said first and second pacemaker terminals, respectively.

11. The pacemaker connector assembly as set forth in claim 10, wherein said first and second conductive means comprise first and second ribbon conductors, respectively, a portion of each ribbon conductor protruding out from the body tip or body ring in which the ribbon conductor is molded.

12. The pacemaker connector assembly as set forth in claim 11, wherein said means for making respective electrical contact between said first and second ribbon conductors and said first and second pacemaker terminals includes an epoxy cast that maintains the protruding portions of said first and second ribbon conductors in a spaced apart relationship.

13. A method of making a molded pacemaker connector comprising:
   (a) forming a hoop in a first end of a first electrical conductor, said hoop having a diameter less than a precision diameter required in said pacemaker connector;
   (b) expanding said hoop end of said first electrical conductor over a precision core pin within a connector mold, said precision core pin having a diameter equal to said precision diameter;
   (c) injecting a non-conductive polymer into said connector mold while said polymer is in a liquid state, and allowing said polymer to cure to assume a solid state; and
   (d) removing said cured polymer, including said first electrical conductor, from said connector mold, said hoop end of said electrical conductor being held to said precision inner diameter by said cured polymer, a second end of said first electrical conductor protruding out from said cured polymer;
   said cured polymer, including said hoop end of said electrical conductor molded therein comprising said molded pacemaker connector.

14. The method of making a molded pacemaker connector as set forth in claim 13 further including inserting a garter spring into said cured polymer so as to make physical contact with an inner surface of said hoop, said garter spring being made from an electrically conductive material, said garter spring thereby providing a means for making electrical contact between said first electrical conductor and the circumference of an electrode of a pacemaker lead inserted into said pacemaker connector so as to pass through said garter spring.

15. The method of making a molded pacemaker connector as set forth in claim 14 further including inserting a first sealing means within said molded pacemaker connecter to seal said garter spring and hoop from coming in contact with fluids to which said molded pacemaker connector is externally exposed.

16. The method of making a molded pacemaker connector as set forth in claim 15 further including:
   attaching a second electrical conductor to a connector block adapted to receive a tip electrode of a pacemaker lead;
   inserting said connector block, with said second electrical conductor attached thereto, into a second connector mold;
   injecting said non-conductive polymer into said second connector mold while said polymer is in a liquid state, and allowing said polymer to cure to assume a solid state;
   removing said cured polymer, including said connector block and second electrical conductor, from said second connector mold, the detached end of said second electrical conductor protruding out from said cured polymer, said cured polymer and said connector block molded therein comprising a tip connector;
   inserting a second sealing means within said tip connector; and
   joining said tip connector to said molded pacemaker connector.

17. The method of making a molded pacemaker connector as set forth in claim 16 further including testing said molded pacemaker connector for leakage and dimensionality.

18. The method of making a molded pacemaker connector as set forth in claim 17 further including:
   connecting said protruding ends of said first and second electrical conductors to respective terminals of a sealed pacemaker; and
   casting said tested molded pacemaker connector in an epoxy header assembly that is bonded to said sealed pacemaker.

19. The method of making a molded pacemaker connector as set forth in claim 16, wherein said non-conductive polymer comprises polysulfone.

20. The method of making a molded pacemaker connector as set forth in claim 19 further including making said first and second sealing means as an annular ring made from a flexible silicon elastomer, each annular ring having a plurality of circumferential ridges adapted to make sealing contact with the circumference of a pacemaker lead inserted into said molded pacemaker connector.

* * * * *